US009949815B2

(12) United States Patent
Priewe (10) Patent No.: US 9,949,815 B2
(45) Date of Patent: Apr. 24, 2018

(54) SURGICAL IMPLANT

(71) Applicant: Johnson & Johnson Medical GmbH, Somerville, NJ (US)

(72) Inventor: Joerg Priewe, Norderstedt (DE)

(73) Assignee: Johnson & Johnson GMBH, Norderstedt (DE)

( * ) Notice: Subject to any disclaimer, the term of this patent is extended or adjusted under 35 U.S.C. 154(b) by 184 days.

(21) Appl. No.: 14/385,300

(22) PCT Filed: Mar. 21, 2013

(86) PCT No.: PCT/EP2013/000868
§ 371 (c)(1),
(2) Date: Sep. 15, 2014

(87) PCT Pub. No.: WO2013/139482
PCT Pub. Date: Sep. 26, 2013

(65) Prior Publication Data
US 2015/0066063 A1    Mar. 5, 2015

(30) Foreign Application Priority Data
Mar. 23, 2012  (DE) .................. 10 2012 005 978

(51) Int. Cl.
*A61B 17/08* (2006.01)
*A61F 2/00* (2006.01)

(52) U.S. Cl.
CPC .... *A61F 2/0063* (2013.01); *A61F 2002/0068* (2013.01); *A61F 2220/0016* (2013.01)

(58) Field of Classification Search
CPC .. A61F 2002/0068; A61F 2/0063; A61F 2/82; A61F 2/848; A61F 2/86; A61F 2/105; A61F 2/0031; A61F 2220/0016; A61F 2220/00; A61B 2017/081; D10B 2509/08; D10B 2403/0213; D10B 2501/0632
USPC .......................... 428/221, 151; 606/151, 213
See application file for complete search history.

(56) References Cited

U.S. PATENT DOCUMENTS

| 5,397,355 A * | 3/1995 | Marin ................ A61F 2/91 623/1.2 |
| 7,331,199 B2 | 2/2008 | Ory et al. |
| 2005/0182477 A1* | 8/2005 | White ................ A61F 2/82 623/1.15 |
| 2011/0288566 A1* | 11/2011 | Kubiak ................ A61F 2/08 606/151 |
| 2012/0016388 A1 | 1/2012 | Houard et al. |

FOREIGN PATENT DOCUMENTS

| EP | 2368524 | 9/2011 |
| WO | WO 2003/099160 | 12/2003 |
| WO | WO 2010/086515 | 8/2010 |

* cited by examiner

*Primary Examiner* — Diane Yabut
*Assistant Examiner* — Erich Herbermann
(74) *Attorney, Agent, or Firm* — E. Richard Skula (57) ABSTRACT

A surgical implant (10) has an areal basic structure (12) provided with pores (14). At least one projection (16, 17), which emerges at an angle of at most 40° from the plane defined by the areal basic structure (12) in the local environment of the projection (16, 17), protrudes into at least one of the pores (14). Preferably, the at least one projection (16, 17) is produced from material of the basic structure (12), starts from the edge of the pore (14) and lies in the area defined by the basic structure (12).

19 Claims, 5 Drawing Sheets

SURGICAL IMPLANT

CROSS REFERENCE TO RELATED APPLICATIONS

The present application is the National Stage filing of International Application PCT/EP2013/000868 filed Mar. 21, 2013 which claims priority to German Patent Application DE 102012005978.7 filed Mar. 23, 2012, the disclosure of which is hereby incorporated by reference in its entirety.

The invention relates to a surgical implant with an areal basic structure provided with pores.

Surgical implants for soft body tissue, for example hernia implants, are often difficult to position at the intended location. Fixing means such as staples or sutures are usually necessary to hold the implant in a flat or areal deployed state and to prevent it from moving in the body tissue before it has become incorporated. This can lead to complications in the surgical operation or can cause side effects.

WO 2003/099160 A1 discloses a medical implant in the form of a knobbed film. The knobs give the implant greater flexibility.

WO 2010/086515 A1 discloses an implantable plate with a textile substrate, which plate is provided, on at least one of its surfaces, with a number of projections intended to prevent slipping of the implant. These projections are produced by punching, one perforation being formed in each case at the centre of an embankment-shaped projection. The projections jut out from the plane of the plate at an angle in the range of 45° to 90°.

U.S. Pat. No. 7,331,199 discloses a textile implant with projections that protrude perpendicularly with respect to the implant plane, with a head sitting at the free ends of each of the projections.

EP 2 368 524 A2 discloses a surgical implant comprising a substrate, of which the surface is provided with projections made from a memory material. When the implant is fitted, the projections are completely flat. A change of temperature causes the projections to bend upwards at steep angles in order to anchor the implant in the body tissue.

The object of the invention is to provide a surgical implant that automatically fixes itself at least partially in the body tissue and that can be easily produced.

This object is achieved by a surgical implant having the features of claim 1. Advantageous embodiments of the invention are set forth in the dependent claims.

The surgical implant according to the invention comprises an areal basic structure provided with pores. At least one projection protrudes into at least one of the pores. From the plane defined by the areal basic structure in the local environment of the projection, the projection emerges at an angle $\alpha$ of at most 40°. The maximum value of the angle $\alpha$ can also be given by any smaller value than 40°, in particular by one of the values contained in the following list: 38°, 36°, 34°, 32°, 30°, 28°, 26°, 24°, 22°, 20°, 18°, 16°, 14°, 12°, 10°, 8°, 6°, 4°, 2°.

In advantageous embodiments of the invention, the at least one projection lies in the area defined by the basic structure, i.e. the angle $\alpha$ is very small, practically zero, or zero, as long as the projection is not bent.

The basic structure is areal in the sense that its thickness is generally small (e.g. less than 1 mm) compared to its extent in the length direction and width direction (e.g. more than 1 mm and in most cases significantly more than 1 mm).

The implant according to the invention is suitable in particular as a hernia mesh, but other uses are likewise conceivable, including as part of a medical implant that has further components. In principle, the implant is conceived for implantation in tissue of humans or mammals.

The pores of the basic structure can in principle have any shape and can be arranged in any pattern. The shape and the arrangement of the pores give the basic structure elasticity and adaptability to the anatomical circumstances at the implantation site.

One or more projections protrude into a given pore of the basic structure, although it is also possible for no projection to protrude into a given pore. Generally, a number of pores of the basic structure are provided with one or more projections. The individual projections can be differently configured and/or extend in different directions.

The projections increase the friction when an attempt is made to pull the implant across body tissue, particularly when it is pulled in the direction of the free end of a projection, since the free end can then hook or fix itself at least temporarily on the body tissue. If a number of projections are present, the frictional behaviour of the basic structure can be predefined by the directions of the projections (see also below). With the aid of the projections, the implant according to the invention thus fixes itself substantially automatically on the body tissue, at least in directions predetermined by the orientation of the projections.

Therefore, during the operation for fitting the implant according to the invention in place, it is possible to do without fixing means such as sutures or staples, thereby speeding up the course of the operation. In the initial phase after the operation, tissue can pass through the pores of the basic structure, without obstruction by additional fixing means, such that the implant becomes well incorporated and can fulfil its actual purpose, namely that of supporting the treated body tissue.

In advantageous embodiments of the invention, the at least one projection is produced from material of the basic structure and starts from the edge of the pore. Thus, the at least one projection can be made in one piece with the basic structure, e.g. by being cut out from the basic structure. It is particularly advantageous if the basic structure is designed as a film, from which the pores are cut out in such a way as to leave the projections protruding into the pores. The term "cut out" is to be understood here in the geometric sense and is not limited to a cutting technique. Implants of this kind are easy to produce and can be used as implants similar to an implant mesh. The stretch behaviour of the basic structure is particularly favourable if the basic structure, opposite the location where the at least one projection starts from the edge of the pore, has a recess, which is preferably designed as part of a pore adjacent to the pore.

The size of the pores can be at least 1 mm. The "size" of a pore is to be understood as a typical length measurement, e.g. the side length in the case of a substantially square pore, and the length of the longer side in the case of a rectangular pore, which in any case is not too long in practice. A projection can have a length that is at least half as great as the size of the pore into which it protrudes. The length of a projection is, for example, at least 1 mm. Pores and projections of such sizes are easy to produce and show the desired effect on the implant.

In preferred embodiments of the implant according to the invention, the at least one projection tapers in the direction of its free end. In projections shaped in this way, the friction effect increases if the implant is pulled across body tissue in the direction of the free ends of the projections. However, the free ends of the projections must not be tapered to such an extent that surgical gloves are damaged during handling of the implant. Damage to gloves can also be avoided if the projections are made of relatively soft material.

In advantageous embodiments of the implant, as has already been indicated, a multiplicity of pores are provided, each with at least one projection. If each projection has an oriented longitudinal axis, which follows the course of the projection to its free end, the longitudinal axes of all the projections in the implant can extend in one direction or in at least two different directions.

Embodiments with only one direction of the projections lead to substantial self-fixing of the implant against pulling in one direction. If the projections point in different directions, they can be arranged in patterns. An example of this is a group of pores substantially following the course of the circumference of a circle, with the projections pointing to the centre of this circle. Generally, in pores differing from one another, the projections can extend in different areas of the pores. A number of examples of the many possibilities are explained in more detail below.

Depending on the implant, it can also be advantageous if the projections are arranged only in some zones of the implant. Examples of this are implants in which pores in an edge zone of the implant are provided with projections, whereas no projections are present in a central zone of the implant.

In an advantageous embodiment of the implant according to the invention, as has already been indicated, the basic structure is designed as a film (preferably not of metal), in particular as a polymer film. However, areal structures for the basic structure can also be differently configured, e.g. as polymer foam or as textile fabric, in particular as woven, knitted or crocheted fabric. Nonwoven materials (here designated as polymeric nonwovens, although this is not to be understood in a restrictive sense) are likewise conceivable.

It is also possible to use laminates of several areal structures, with identical types (e.g. film on film) and also with different types (e.g. film on knit) of the aforementioned areal structures.

In advantageous embodiments of the invention, the at least one projection is strengthened, e.g. with a coating or by thermoforming. A coating can, for example, be applied locally to a basic structure which is designed as a film and from which the pores with projections are cut out, e.g. applied only to the projections and, if appropriate, also in the start area of the projections. A material thickening in the area of the projections can also be achieved by thermoforming.

In principle, the areal basic structure can have a great many shapes. For example, in addition to square, round or compact rectangular shapes, it is also possible to consider using elongate shapes, in particular shapes in which the length of the basic structure is at least three times as great as the width. Implants of this kind can be used as implant strips and, and in the case of very elongate shapes, also as surgical suture material.

Many materials can be considered for use as the material for the basic structure, e.g. preferably polymers. These can be synthetic or biologically generated, resorbable or non-resorbable polymer materials.

Examples of non-resorbable polymers are: polyalkenes, polypropylene, polyethylene, partially halogenated polyolefins, fully halogenated polyolefins, fluorinated polyolefins, polytetrafluoroethylene, polyvinylidene fluoride, polyisoprenes, polystyrenes, polysilicones, polycarbonates, polyaryletherketones, polyurethanes, polymethacrylates, polyacrylates, polyimides, hydrophilic crosslinked polymers, and silicones, and also copolymers of polymerizable substances thereof.

Examples of resorbable polymers are: polyhydroxy acids, polylactides, polyglycolides, polyhydroxybutyrates, polyhydroxyvalerates, polycaprolactones, poly-dioxanones, synthetic and natural oligo and polyamino acids, polyphosphazenes, polyanhydrides, polyortho-esters, polyphosphates, polyphosphonates, polyalcohols, polysugars, polyethers, polyamides, aliphatic polyesters, aromatic polyesters, natural polyamino acids, synthetic polyamino acids, genetically engineered polyamino acids, collagen, rh-collagen, silk, pseudo-polyamino acids, polycyanoacrylates, polyethylene glycols, polyvinyl alcohols, derivatized cellulose, polyphosphate esters, and also copolymers of polymerizable substances thereof. Resorbable glasses may also be used.

It is also conceivable to use different materials, including the simultaneous use of non-resorbable and resorbable materials.

In advantageous embodiments of the invention, the basic structure contains different materials, of which at least one is resorbable, and the at least one projection has this resorbable material. In implants of this kind, the degradation profile over time can be specifically defined. For example, the projections may be degraded more rapidly than the rest of the basic structure, since the projections are often only needed at the start of the healing process, for as long as sufficient body tissue has not yet grown through the implant.

The implant can also have additional barbs, which are not formed from the projections discussed above. Additional barbs can, for example, be applied as add-on parts to the basic structure.

In many embodiments of the implant according to the invention, the implant consists principally of the basic structure and of the projections protruding into the pores, which projections can be made from the material of the basic structure. In other embodiments, the implant is used as part of a medical implant that has further components.

An example of this is a film with pores, from which film the projections are formed and which is connected to an additional implant mesh that in this case contributes substantially to the mechanical properties of the implant. In this case, it is conceivable to cover both sides of the additional implant mesh with a film having pores and projections. It is thus possible for several implants, each with a basic structure and projections, to be used on a larger medical implant. In addition to implant meshes, other examples of medical implants of this kind are: catheters, tubes, breast implants, and so on. In all these cases, the projections can contribute to rapid and secure fixing of the medical implant at its desired location.

Several methods are described below for producing a surgical implant according to the invention which has an areal basic structure with pores (holes) and projections.

In cutting methods, the pores are cut out from an areal structure (e.g. a sheet or a film), in which methods the at least one projection protruding into a respective pore and starting from the edge of the pore is not cut away. Conventional cutting methods are laser cutting, water jet cutting, ultrasonic cutting, plasma cutting, mechanical cutting, thermal cutting, punching and micro-milling. On account of a melting process in the area of the cut line, laser cutting methods can also lead to a partial thickening and therefore stiffening of the projection.

In moulding methods, a suitable mould is first produced. The mould is filled with liquid plastic (melt or solution), which thereafter hardens or is hardened. This category also includes injection moulding methods.

Further methods that may be mentioned are polymerization in a mould, remelting in a mould with energy supply, and printing techniques in which, for example, a strengthening layer is printed onto the projections.

As has already been indicated, examples of possible areal structures for the basic structure are polymer films (preferably biaxially stretched films or sheets), foams, nonwovens, or condensed textiles (e.g. cPTFE or condensed ePTFE). Fibre-reinforced composite films can also be used. For example, a woven "Vicryl" membrane ("Vicryl": copolymer of lactide and glycolide) can be coated with a polylactide-co-glycolide from a suitable solvent such as acetone, ethyl acetate or dichloromethane; if the solvent is evaporated off, a resorbable polymer film is obtained which is strengthened by a resorbable textile; this composite film can also be provided with pores (holes) and recesses by the methods discussed.

Implants according to the invention can also be produced from biological material in accordance with the invention, e.g. by means of collagen, for example, being poured into a suitable mould, dried and optionally cut out. It is also possible to machine biological implants, e.g. "Surgisis" (Cook) or "Strattice" (LifeCell), using the punching or cutting methods mentioned above.

An implant in which the projections degrade differently than the basic structure after implantation can be produced in the following way for example: The basic structure is an areal structure with regular pores (e.g. hexagonal, round, rhomboid), which is produced first. In a second step, the projections are added in part (as toothed projections), by means of the areal structure being placed in a toothed-projection mould and dripped onto in the area of the teeth with a polymer solution or melt. Depending on the material, the tooth-shaped projections have a different mechanical behaviour or degradation behaviour.

If a surgical implant according to the invention is to be used as part of a medical implant with further components (e.g. a conventional hernia mesh), customary joining techniques are suitable for connection to the other components, for example adhesive bonding, ultrasonic welding, plasma welding, laminating, sewing and/or embroidering.

The invention is described in more detail below on the basis of illustrative embodiments. In the figures.

Figure 1:
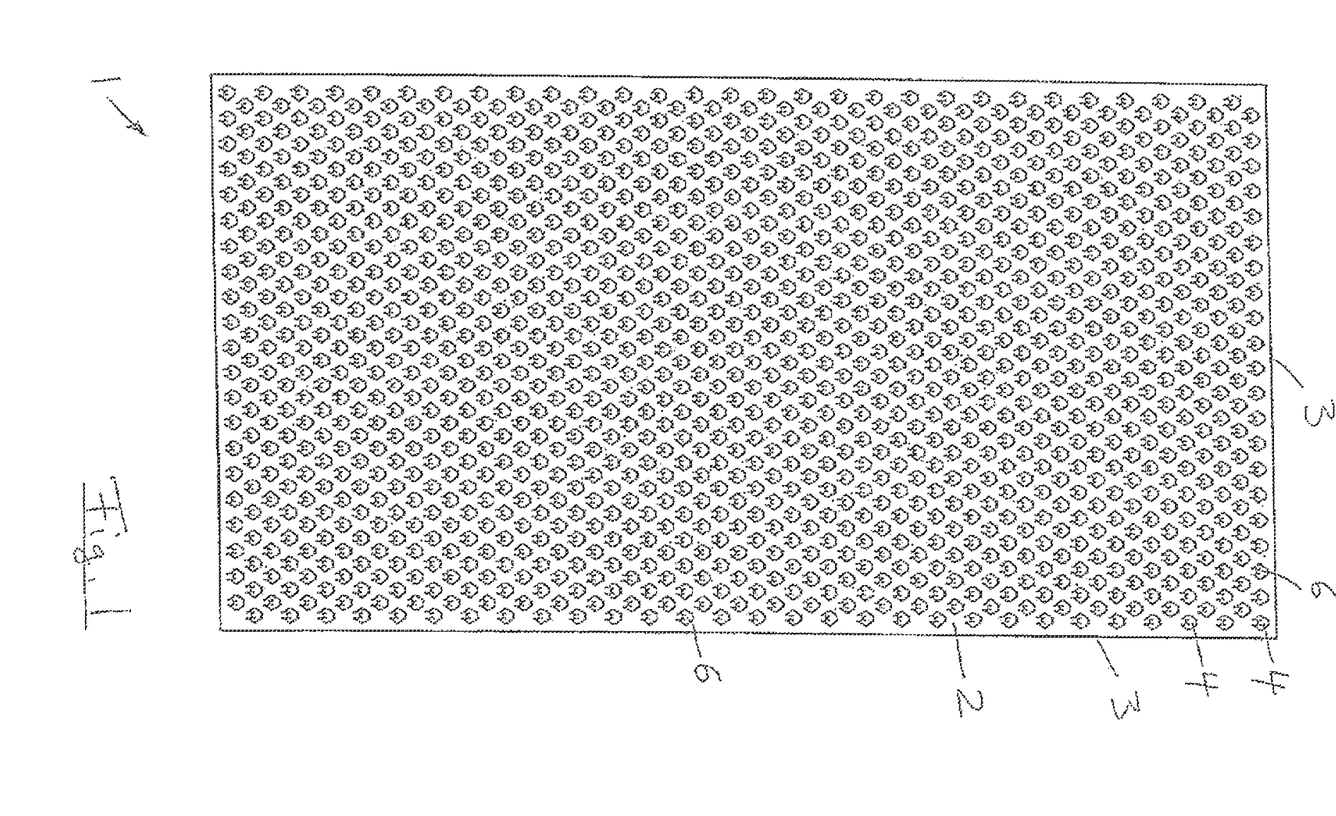
FIG. 1 shows an overall view of an embodiment of the surgical implant according to the invention in a plan view, approximately to the original size.

In FIG. 1, an embodiment of a surgical implant 1 is shown in a plan view, approximately to the original size.

The implant 1 has a rectangular basic structure 2 with an edge 3, and the basic structure 2, in the illustrative embodiment, is produced from a film. A plurality of pores 4 are cut out from the area of the basic structure 2. A projection 6 protrudes into each of these pores 4 and, in the illustrative embodiment, is designed as a double projection (or two projections), starts from the edge of the pores 4 and extends in the plane of the basic structure 2 (unless it is bent). A pore of the implant 1 with its double projection appears, in an enlarged view, as shown in FIG. 5(b). In the implant 1, the projections 6 are oriented parallel to one another, i.e. they all extend in the same direction.

Figure 2:
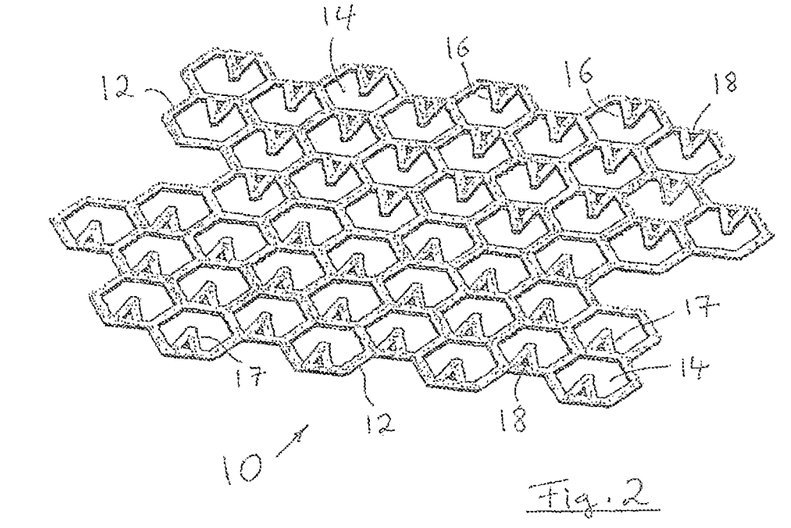
FIG. 2 shows an enlarged detail of another embodiment of the implant according to the invention in an oblique view.

FIG. 2 shows a detail of a further implant 10 in an oblique view. The implant 10 contains a basic structure 12 provided with hexagonal pores 14, into each of which a projection 16 or a projection 17 protrudes. The projections 16 and 17 are oriented antiparallel to one another, i.e. their tapered free ends point in diametrically opposite directions. Each of the projections 16, 17 has a triangular recess 18.

Figure 3:
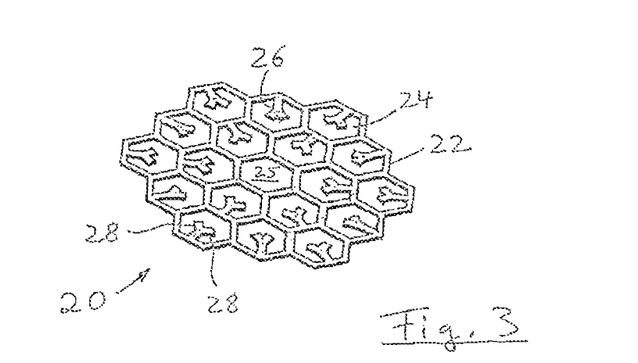
FIG. 3 shows an enlarged detail of another embodiment of the implant according to the invention in an oblique view.

FIG. 3 shows a detail of a further implant 20, again in an oblique view. The implant 20 has a basic structure 22 provided with hexagonal pores 24, of which the central pore is designated by 25. The arrangement of pores 24, 25 shown in FIG. 3 is repeated across the implant 20, since hexagonal arrangements of this kind make it possible to fill up an area without leaving gaps. As can be seen in FIG. 3, a projection starting from the edge of the pore 24 and having two protuberances 28 at the free end protrudes into each of the pores 24. The projections 26 are all directed toward the central pore 25, and there is no projection protruding into the central pore itself. The directions of the projections 26 are therefore different. This provides effective fixing of the implant 20 against slipping in all directions.

Figure 4:
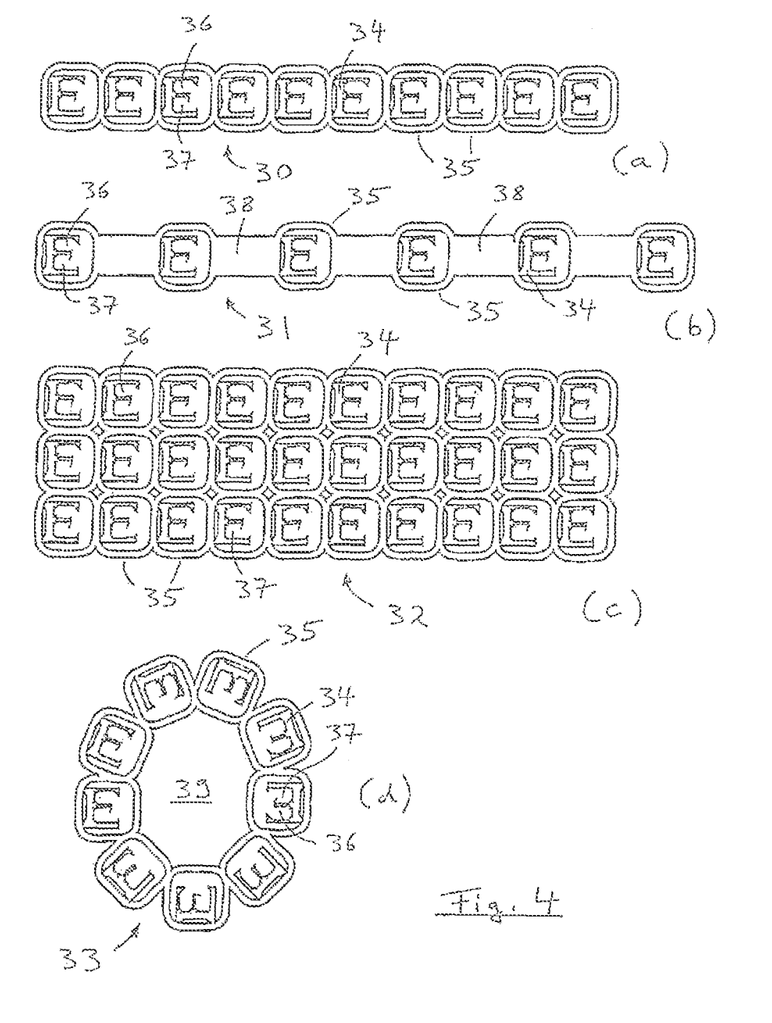
FIG. 4 shows, in parts (a) to (d), plan views of other embodiments of the implant according to the invention.

FIG. 4 shows, in parts (a), (b), (c) and (d), four implants 30, 31, 32 and 33, respectively, which are all constructed from similarly designed sections. Each of these sections contains a pore 34 in an area 35 of the basic structure. Two projections 36, 37 with rounded free ends protrude into each of the pores 34. The open area of each pore 34 thus obtains the shape of a letter "E".

The implants 30 and 31 according to FIGS. 4(a) and 4(b), respectively, are elongate, and the implant 31 is provided with a connecting bridge 38 between in each case two adjacent sections with pores 34. The implant 32 according to FIG. 4(c) is rectangular. In the implant 33 according to FIG. 4(d), the sections with the pores 34 are arranged like a circle, the implant 33 having a larger central recess 39.

Figure 5:
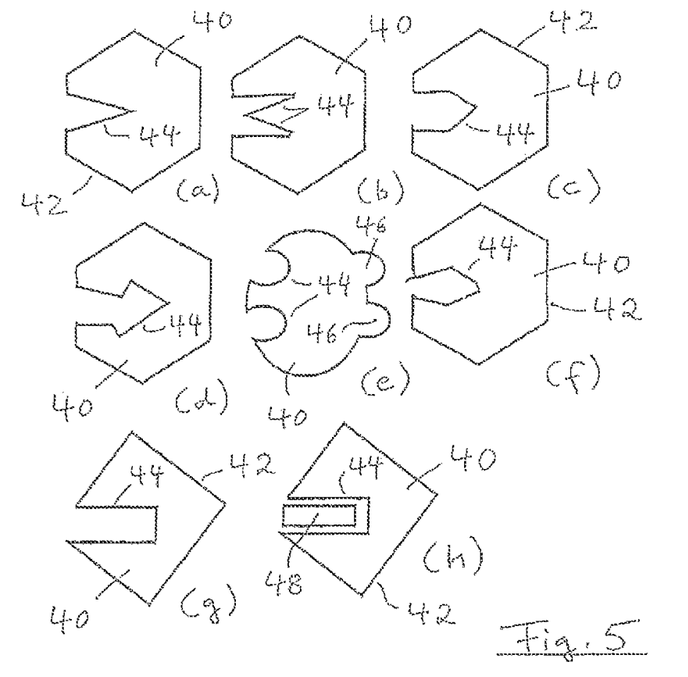
FIG. 5 shows, in parts (a) to (h), schematic views of examples of different pore shapes in implants according to the invention, with one or two projections being provided in each case.

FIG. 5 shows, in parts (a) to (h), further illustrative embodiments of pores, into each of which there protrudes at least one projection. For simplicity, all the pores are designated here by 40, their edges by 42, and the projections by 44. The projections 44 each start from the edge 42 of a pore 40. In the illustrative embodiment according to FIG. 5(b), there are two projections or a double projection (see also FIG. 1). The same applies to the illustrative embodiment according to FIG. 5(e), in which case the pore 40 is further extended by two recesses 46 (in this connection, see also the illustrative embodiment according to FIG. 7). In the case of the illustrative embodiment according to FIG. 5(h), a recess 48 is located within the projection, as a result of which the projection is effectively made softer. Many other forms of pores with projections are likewise possible.

Figure 6:
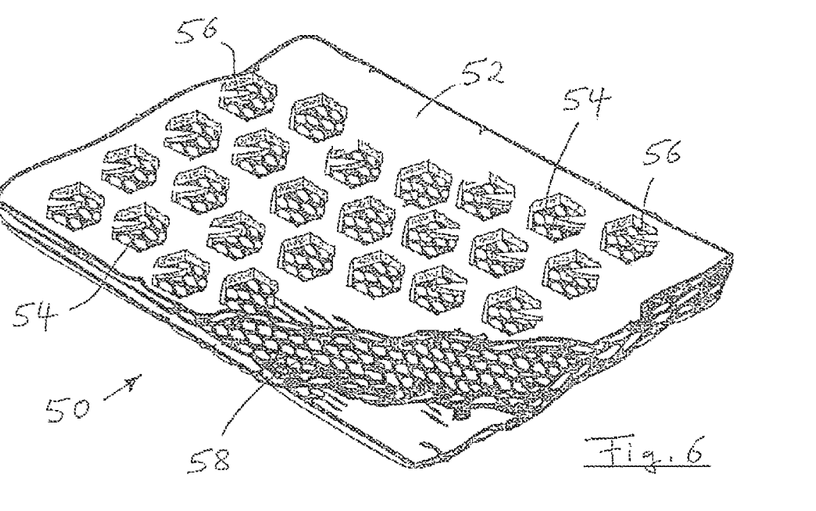
FIG. 6 shows an enlarged detail of an embodiment of a medical implant in which an implant according to the invention is connected to a conventional implant mesh, in a schematic three-dimensional view.

FIG. 6 shows an enlarged detail of a medical implant 50, which is constructed from two parts. Lying at the top in FIG. 6, and shown partially cut away, there is a basic structure 52 produced from a film and having pores 54, into some of which a projection 56 partially protrudes. The projections 56 are tapered and are arranged in two groups with diametrically opposite directions. This first part corresponds to an implant of the type explained above. Lying underneath in FIG. 6, and more clearly visible because part of the basic structure 52 has been cut away, there is a conventional implant mesh 58 as second part of the medical implant 50. The implant mesh 58, which is joined to the basic structure 52 by sewing for example, chiefly determines the mechanical properties of the medical implant 50, while the basic structure 52 with the projections 56 facilitates fixing.

There follow further consecutively numbered examples of specific embodiments.

EXAMPLE 1

A laser (CadCam) was used to cut a pore structure from an approximately 120 μm thick, rectangular film of polypropylene measuring 10 cm×15 cm and serving as basic structure. The pores each had a hexagonal basic shape with a height of 3 mm and a width of 2 mm, and a triangular and flat projection having a length of approximately 1.1 mm, and starting from the right-hand pore edge (in the view according to FIG. 7), protruded into each pore. On the opposite pore side, a triangular recess with a length of approximately 1.4 mm was cut out in each case.

Figures 7, 8:
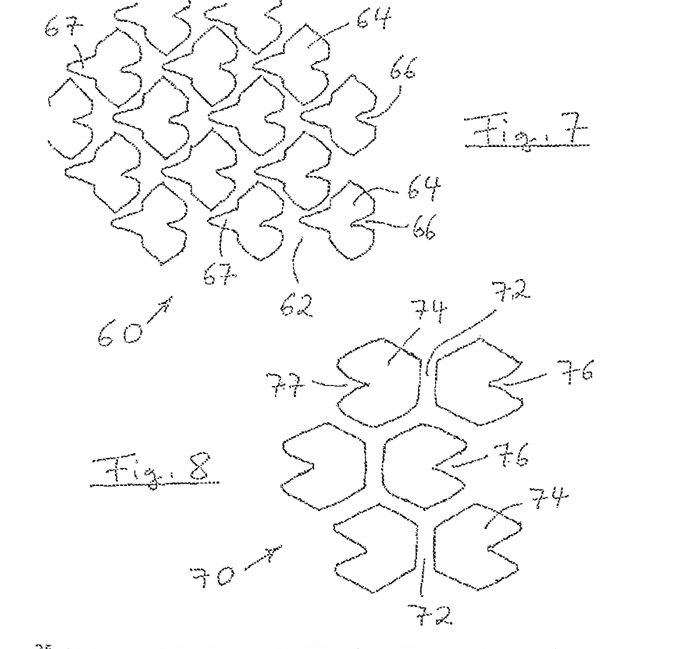
FIG. 7 shows an enlarged detail of another embodiment of the implant according to the invention in a plan view.
FIG. 8 shows an enlarged detail of another embodiment of the implant according to the invention in a plan view.

The result is shown in FIG. 7, in which the implant is designated by 60, the basic structure by 62, the pores by 64, and the projections by 66, while the triangular recesses lying opposite each of the projections and issuing from a respective adjacent pore are designated by 67. The flexibility of the basic structure 62 is increased by the recesses 67.

EXAMPLE 2

A laser (CadCam) was used to cut a pore structure from an approximately 120 μm thick, rectangular film of polypropylene measuring 10 cm×15 cm and serving as basic structure. The pores each had a hexagonal basic shape with a height of 3 mm and a width of 3 mm. A triangular and flat projection having a length of approximately 1.1 mm protruded into each pore. In the pores on the right-hand side of the implant (in the view according to FIG. 8), the projections started from the right-hand pore edge, and in the pores on the left-hand side of the implant, the projections started from the left-hand pore edge. Thus, the free ends of the projections each pointed towards the centre of the implant, i.e. towards a central axis.

A detail of this implant is shown in FIG. 8, in which the implant is designated by 70, the basic structure by 72, the pores by 74, and the projections by 76 and 77. The projections 76 on the right-hand side of the implant point towards the left, while the projections 77 on the left-hand side point towards the right.

As a result of a melting process in the area of the cut line, laser cutting techniques can lead to a partial thickening and therefore stiffening of the projections. Thus, in Examples 1 and 2, the lengths of the projections were approximately 1.0 mm to 1.3 mm, i.e. slightly less than could be expected from the original laser pattern with 1.5 mm. The melting process can also cause a partial deformation of the projections, e.g. a partial lifting at the free ends, or changes to the surface, all of which can lead to an improvement of the implant properties.

EXAMPLE 3

The implants from Example 1 and Example 2 were tested in the rat skin friction model as per WO 2006/092236 A1. A film analogous to Example 2, with pores of hexagonal shape having a height of 3 mm and a width of 3 mm, but with no projections, served for comparison.

Figure 9:
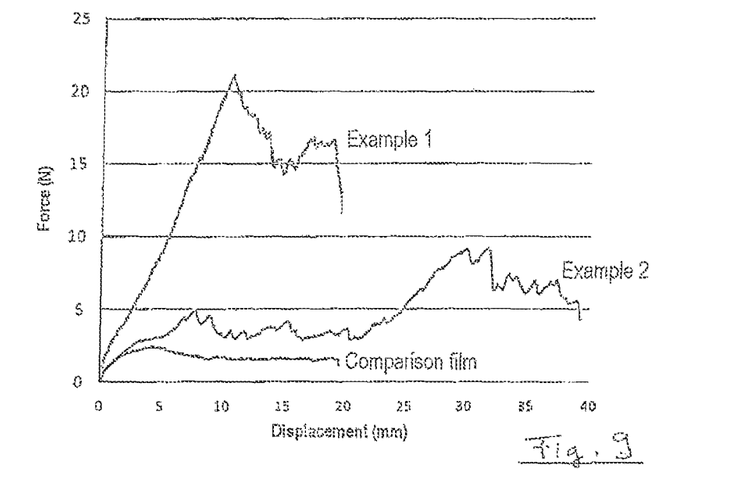
FIG. 9 shows a diagram illustrating the forces occurring on rat skin upon displacement of the embodiments according to FIG. 7 and FIG. 8 and of a conventional comparison implant.

The results for the three tested implants are shown in FIG. 9, in which the measured frictional force (in N) is in each case plotted over the displacement path (in mm).

The implant from Example 1 (all projections in one direction) showed a sharp increase in force from the outset up to approximately 20 N, when the rat skin was moved against the direction of the projections. The increase is explained by the fact that, under the given test conditions, more and more projections came into contact with the rat skin as displacement increased, until this applied to all the projections.

The implant from Example 2 (projections in opposite directions) was initially moved relative to the rat skin counter to the direction of the projections, such that the projections showed little effect and the frictional behaviour largely corresponded to the comparison film. Only when the projections came into contact with the rat skin with their free ends leading did the force increase sharply to approximately 10 N.

EXAMPLE 4

The implant from Example 1 was placed in different layers of pork belly (fat contact and muscle contact). Slight pressure without pulling already resulted in a locking of the basic structure. With a pulling direction against the projections, the implant was fixed.

With pulling in the opposite direction, the implant was released again. There was good adherence in different tissue (fat and muscle).

EXAMPLE 5

A further implant was produced analogously to Example 1, but the material used for the basic structure was a 150 μm thick film from the resorbable material poly-p-dioxanone. The implant showed good adherence in the rat skin test (analogously to Example 3).

EXAMPLE 6

Analogously to WO 2011/159700 A1, a medical implant was produced as laminate with a conventional surgical polypropylene mesh between two 20 μm thick sheets of a polyglycolide-co-caprolactone. A perforated film of poly-p-dioxanone, ca. 8 μm thick, served as hot-melt adhesive. The two sheets of polyglycolide-co-caprolactone had pores and projections according to Example 2, with a hexagonal basic shape measuring 3 mm×3 mm, and with triangular projections which measured approximately 1.0 mm to 1.5 mm in length and which all pointed in one direction.

The invention claimed is:

1. A surgical implant, comprising a flat basic structure defining a flat plane, the structure provided with a plurality of pores, said pores being in said flat plane, each pore having a plane defined by the basic structure surrounded by edges, wherein at least one pore has a projection that starts from an edge and protrudes into and lies entirely in the plane of the pore, wherein the structure has a shape selected from the group consisting of rectangular, square, round and elongated, wherein the implant is configured to be implanted as a flat basic structure, and wherein the implant automatically affixes itself to body tissue.

2. The implant according to claim 1, characterized in that the at least one projection is made from material of the basic structure and starts from the edge of the pore.

3. The implant according to claim 2, characterized in that the basic structure, opposite the location where the at least one projection starts from the edge of the pore, has a recess, which is preferably designed as part of a pore adjacent to the pore.

4. The implant according to claim 1, characterized in that the size of the pores is at least 1 mm.

5. The implant according to claim 1, characterized in that the at least one projection has a length that is at least half as long as the size of the pore.

6. The implant according to claim 1, characterized in that the length of the at least one projection is at least 1 mm.

7. The implant according to claim 1, characterized in that the at least one projection tapers in the direction of its free end.

8. The implant according to claim 1, characterized in that a plurality of pores is provided with at least one projection each.

9. The implant according to claim 8, characterized in that each projection has an oriented longitudinal axis, which follows the course of the projection to its free end, and in that the longitudinal axes of all the projections in the implant extend in one direction or in at least two different directions.

10. The implant according to claim 1, characterized in that the flat basic structure comprises an areal structure selected from the group consisting of films, polymer films, polymer foams, polymer nonwovens, wovens, warp-knits, weft-knits, crochets, and laminates.

11. The implant according to claim 1, characterized in that the at least one projection is strengthened, preferably with a coating or by thermoforming.

12. The implant according to claim 1, characterized in that the at least one projection is designed in one piece with the basic structure, and the at least one projection is cut out from the basic structure.

13. The implant according to claim 1, characterized in that pores in an edge zone of the implant are provided with projections, while a central zone of the implant is not provided with projections.

14. The implant according to claim 1, characterized in that the basic structure has a length and a width, the length being at least three times as long as the width.

15. The implant according to claim 1, characterized in that the basic structure comprises different materials, of which at least one is resorbable, and the at least one projection comprising the last-mentioned material.

16. The implant according to claim 1, characterized in that the basic structure comprises at least one of the materials chosen from the following list: polyalkenes, polypropylene, polyethylene, partially halogenated polyolefins, fully halogenated polyolefins, fluorinated polyolefins, polytetrafluoroethylene, polyvinylidene fluoride, polyisoprenes, polystyrenes, polysilicones, polycarbonates, polyaryletherketones, polyurethanes, polymethacrylates, polyacrylates, polyimides, hydrophilic cross-linked polymers, silicones; polyhydroxy acids, polylactides, polyglycolides, polyhydroxybutyrates, polyhydroxy-valerates, polycaprolactones, polydioxanones, synthetic and natural oligo and polyamino acids, polyphosphazenes, polyanhydrides, polyorthoesters, polyphosphates, polyphosphonates, polyalcohols, polysugars, polyethers, polyamides, aliphatic polyesters, aromatic polyesters, natural polyamino acids, synthetic polyamino acids, genetically engineered polyamino acids, collagen, rh-collagen, silk, pseudo-polyamino acids, polycyanoacrylates, polyethylene glycols, polyvinyl alcohols, derivatized cellulose, polyphosphate esters; copolymers of polymerizable substances from the above list; resorbable glasses.

17. The implant according to claim 1, characterized in that the implant comprises additional barbs.

18. The implant according to claim 1, characterized in that the implant is designed as a soft-tissue implant comprising a polymer and is adapted to fix itself at least partially in soft tissue such as muscle or fat, with the friction between the implant and the soft tissue being increased in at least one direction.

19. A method of using the surgical implant of claim 1 comprising the step of automatically affixing said implant to tissue by placing the implant on tissue.

\* \* \* \* \*